(12) United States Patent
Delcroix et al.

(10) Patent No.: US 9,617,235 B2
(45) Date of Patent: Apr. 11, 2017

(54) METHOD FOR THE CONVERSION OF LIGNOCELLULOSIC BIOMASSES INTO MONO-OXYGENATED OR POLY-OXYGENATED MOLECULES

(71) Applicant: IFP ENERGIES NOUVELLES, Rueil-Malmaison (FR)

(72) Inventors: Damien Delcroix, Saint-Maurice-l'Exil (FR); Christophe Vallee, Sassenage (FR); Amandine Cabiac, Givors (FR); Emmanuelle Guillon, Vourles (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 0 days.

(21) Appl. No.: 14/903,335

(22) PCT Filed: Jul. 3, 2014

(86) PCT No.: PCT/FR2014/051706
§ 371 (c)(1),
(2) Date: Jan. 7, 2016

(87) PCT Pub. No.: WO2015/004369
PCT Pub. Date: Jan. 15, 2015

(65) Prior Publication Data
US 2016/0376246 A1  Dec. 29, 2016

(30) Foreign Application Priority Data
Jul. 12, 2013 (FR) ...................................... 13 56876

(51) Int. Cl.
| | |
|---|---|
| *C07D 309/06* | (2006.01) |
| *C07D 307/32* | (2006.01) |
| *C07C 29/132* | (2006.01) |
| *C07C 51/00* | (2006.01) |
| *B01J 23/652* | (2006.01) |
| *B01J 37/08* | (2006.01) |
| *B01J 37/18* | (2006.01) |

(52) U.S. Cl.
CPC ........ *C07D 309/06* (2013.01); *B01J 23/6527* (2013.01); *B01J 37/08* (2013.01); *B01J 37/18* (2013.01); *C07C 29/132* (2013.01); *C07C 51/00* (2013.01); *C07D 307/32* (2013.01)

(58) Field of Classification Search
CPC ................................................... C07D 309/06
USPC ........................................................... 549/427
See application file for complete search history.

(56) References Cited

U.S. PATENT DOCUMENTS

| | | |
|---|---|---|
| 8,222,465 B2 | 7/2012 | Kalnes et al. |
| 8,624,058 B2 | 1/2014 | Chambon et al. |
| 2011/0313210 A1 | 12/2011 | Kalnes et al. |
| 2013/0053601 A1 | 2/2013 | Chambon et al. |

FOREIGN PATENT DOCUMENTS

FR    2956114 A1    8/2011

OTHER PUBLICATIONS

International Search Report and Search Opinion from PCT/FR2014/051706 dated Sep. 9, 2014.
Zhijun Tai et al. "Temperature-controlled phase-transfer catalysis for ethylene glycol production from cellulose" (2012), vol. 48, No. 56, pp. 7052.

*Primary Examiner* — Taofiq A Solola
(74) *Attorney, Agent, or Firm* — Millen White Zelano and Branigan, PC; John Sopp; Anthony Zelano

(57) ABSTRACT

The invention relates to a process for transformation of lignocellulosic biomass or cellulose using in a simultaneous manner an original combination of at least two homogeneous catalysts and one or more heterogeneous catalyst(s). The use of these catalysts makes it possible to obtain mono-oxidized or poly-oxidized upgradable products directly and to limit the formation of non-upgradable products. Non-upgradable products are defined as soluble and non-soluble humins, i.e., products of high molecular weight obtained from undesirable condensation reactions of sugars and their derivatives.

15 Claims, No Drawings

METHOD FOR THE CONVERSION OF LIGNOCELLULOSIC BIOMASSES INTO MONO-OXYGENATED OR POLY-OXYGENATED MOLECULES

PRIOR ART

For several years now, there has been a sharp resurgence of interest in the incorporation of products of renewable origin within the fuel and chemistry branches, in addition to or in place of products of fossil origin. One possible method is the conversion of the cellulose that is contained in the lignocellulosic biomass into chemical products or intermediate products, such as products that contain one to six hydroxyl groups, n-propanol, ethylene glycol, propylene glycol, glycerol, 1,2-butanediol, or 1,2-hexanediol.

The term lignocellulosic biomass (LCB) or lignocellulose encompasses multiple components that are present in variable quantities according to the origin thereof: cellulose, hemicellulose, and lignin. Hemicellulose and cellulose constitute the carbohydrate portion of the lignocellulose. These are polymers of sugars (pentoses and hexoses). Lignin is a macromolecule that is rich in phenolic units. Lignocellulosic biomass is defined as, for example, the products that are obtained from forestry operations and the by-products that are obtained from agriculture such as straw, as well as certain dedicated plants with a high agricultural yield such as *Miscanthus* or poplar.

The production of chemical products from lignocellulosic biomass makes it possible both to reduce energy dependence with respect to petroleum and to preserve the environment through the reduction of greenhouse gas emissions without using resources intended for food uses.

The direct transformation of lignocellulosic biomass or cellulose into chemical products or intermediate products, in particular mono-oxidized or poly-oxidized products, is a particularly advantageous method. Direct transformation is defined as the transformation of a stage of lignocellulosic biomass or cellulose, optionally pretreated, into upgradable mono-oxidized or poly-oxidized products.

The upgrading of lignocellulosic biomass or cellulose contained in the biomass by the use of a combination of homogeneous and heterogeneous catalysts is extensively described in the literature.

In particular, the use of a combination of homogeneous catalysts based on Brønsted acid and heterogeneous catalysts has often been described for the transformation of the lignocellulosic biomass or the cellulose.

The patent application WO2013/015990 describes a process for producing polyols and in particular alcohols, organic acids, aldehydes, monosaccharides, polysaccharides, phenolic compounds, carbohydrates, glycerol, proteins and depolymerized lignin, as well as hydrocarbons by the hydrolysis and the hydrogenation of microcrystalline celluloses, paper paste and glucose, in the presence of a catalytic system that comprises a non-supported compound based on tungsten or molybdenum, by itself or in a mixture, and a supported compound based on Pt, Pd, Ru, Rh, Ni, Ir by itself or in a mixture on a solid substrate that is selected from among carbon, $Al_2O_3$, $ZrO_2$, $SiO_2$, MgO, $Ce_xZrO_y$, $TiO_2$, SiC, silica alumina, clays, zeolites, taken by themselves or in a mixture. The non-supported compounds based on tungsten or molybdenum, by itself or in a mixture, are Brønsted acids that are selected from among tungstic acid, molybdic acid, ammonium metatungstate, and heteropoly-anions of tungsten, molybdenum, tungstic acid, molybdic acid, by itself or in a mixture. Said process makes possible the conversion of cellulose into ethylene glycol or into propylene glycol with a high yield and a good selectivity. In the examples illustrating the invention, the non-supported catalysts are the following Brønsted acids: tungstic acid ($WO_3.xH_2O$), phosphotungstic acid ($H_3PW_{12}O_{40}$) and ammonium metatungstate (($NH_4)_6(W_{12}O_{40}).xH_2O$). The supported catalyst is Ni/Norit CA-1 or Pd/C, with the contents of metals being between 0.6 and 5% by weight. The majority products in these examples are ethylene glycol and propylene glycol. The transformation of cellulose is carried out in water at a content of 1% by weight of cellulose/water at 245° C. under 60 bars of $H_2$ (at ambient temperature).

The patent application US2009/0326286 describes the hydrolysis and the hydrogenation of lignocellulosic biomasses into monosaccharides in the presence of a homogeneous catalyst and a heterogeneous catalyst. The homogeneous catalyst is described as an organic or mineral Brønsted acid that is preferably selected from among the acids $H_2SO_4$, $H_3PO_4$, $H_3PO_3$, $H_3PO_2$ and $CH_3COOH$. The heterogeneous catalyst is based on activated carbon or acidic alumina on which is deposited a transition metal that is selected from among ruthenium, nickel, platinum, and palladium at contents of between 0.1% and 5.5% by weight relative to the total mass of heterogeneous catalyst. The products that are formed and the associated yields are not specified.

Sels et al. (Chem. Commun. 2010, 46, 3577-3579) study the transformation of cellulose into hexitols (sorbitol+mannitol) in the presence of a homogeneous catalyst and a heterogeneous catalyst. The homogeneous acid catalysts that are used are the Brønsted acids $H_2SO_4$ and $H_4SiW_{12}O_{40}$. The heterogeneous catalyst is 5% by weight of Ru/C. The conversion of the microcristalline cellulose is respectively 50% and 80% with these two acids for a reaction in water at 190° C. and under 50 bars of $H_2$ for 24 hours ($pH_{(25° C.)}=2$). The associated yields of hexitols are 13% and 48%. The ground cellulose is solubilized more quickly with a total conversion in 1 hour under the same operating conditions and a yield of hexitols of 87%.

With a slightly different stance, Zhang et al. (Chem. Commun., 2012, 48, 7052-7054) combine tungstic acid $H_2WO_4$, not soluble in water at ambient temperature, and the heterogeneous catalyst 5% by weight of Ru/C for the conversion of cellulose into ethylene glycol in water at 245° C. under 60 bars of $H_2$. The particular feature of this system is that tungstic acid solubilizes when hot and changes from heterogeneous to homogeneous when the temperature rises to 245° C. The yield of ethylene glycol reaches 59% with total conversion of the cellulose in 30 minutes.

More recently, C. Liang (Green Chem., 2013, 15, 891-895) describes a combination of catalysts for the production of ethylene glycol from cellulose, in water at 245° C. under 60 bars of $H_2$. The addition of calcium hydroxide $Ca(OH)_2$ in combination with the heterogeneous catalyst CuCr makes it possible to increase the yield of ethylene glycol of the reaction from 5% to 30%. The yield of propylene glycol remains stable around 30-35%.

The patent application US2011/0060148 of BIOeCON International Holding describes a process for conversion of lignocellulosic biomass into polyols making it possible to obtain a high polyol yield and to minimize the formation of by-products. In particular, the process comprises a stage for hydrolysis of cellulose and of lignocellulosic biomasses into glucose, a stage for hydrogenation of glucose that is formed into sorbitol, a stage for dehydration of the polyols that are obtained, and a recovery stage, with said stages being carried out in a hydrated metal salt that is used as a solvent in a hydrated metal salt/lignocellulosic biomass ratio of between 1 and 50, which corresponds to a lignocellulosic biomass/metal salt ratio of between 0.02 and 1. The hydrolysis of the cellulose is carried out in a hydrated metal salt, used as a solvent, selected from among the halides of zinc, calcium, and lithium, by itself or in a mixture and in particular in $ZnCl_2.4H_2O$ that is used as a solvent. The hydrolysis stage is also performed in the presence of an inorganic acid, preferably hydrochloric acid (HCl). The hydrogenation of glucose is also carried out in said hydrated metal salt, used as a solvent, in the presence of an inorganic acid, preferably hydrochloric acid (HCl), and a heterogeneous catalyst that is selected from among the conventional catalysts for hydrogenation of sugars, such as the catalysts Ru/C, Raney nickel, Raney copper, and nickel that is supported on carbon or alumina and preferably in the presence of Ru/C, without specifying the content by mass of metals. The examples illustrate the use as a solvent of the hydrated inorganic salt $ZnCl_2.4H_2O$ in a ratio by mass of $ZnCl_2.4H_2O$/cellulose of 12/1. The maximum conversion of the cellulose thus obtained after 1.5 hours is 100%.

Finally, in 2009, R. Raines (JACS, 2009, 131, 1979-1985) described the transformation of sugars, cellulose, and lignocellulose into 2,5-dimethylfuran in two stages. The first stage is carried out in an ionic liquid medium based on dimethylacetamide-LiCl/[EMIM]Cl ([EMIM][Cl]=1-ethyl-3-methylimidazolium chloride) at 140° C. for 2 hours and is catalyzed by a mixture of the metal salt of chromium trichloride ($CrCl_3$) and hydrochloric acid (HCl), both at 10 mol % relative to cellulose. At the end of this first stage, a stage for purification by steric exclusion chromatography is implemented and makes it possible to eliminate the chloride ions from the medium in such a way as to prevent the poisoning of the catalyst used in the second stage. The second stage can thus take place and involves the transformation of the purified solution in the presence of a copper-based catalyst deposited on Ru/C under hydrogen, in 1-butanol at 220° C. for 10 hours for forming 2,5-dimethylfuran. The thus-described two-stage process makes it possible to obtain a high selectivity of 2,5-dimethylfuran but also leads to the production of a significant quantity of humins.

Except for these last two examples respectively relating to the use of a hydrated metal salt that is used as a solvent and an inorganic acid for hydrolyzing the feedstock, and the use, not simultaneous, in a first stage of a homogeneous catalyst that comprises a metal salt and a second homogeneous catalyst based on Brønsted acid, and then, in a second stage, being performed under conditions different from the first, of a heterogeneous catalyst, there is not described in the literature a process that makes possible a direct transformation of the cellulose or more broadly of the lignocellulosic biomass, optionally pretreated, into mono-oxidized or poly-oxidized upgradable products, by bringing the lignocellulosic biomass simultaneously into contact within the same reaction medium, with a combination of at least two homogeneous catalysts that are different in nature and one or more heterogeneous catalyst(s) of the type of those described in this invention.

The works of the applicant made it possible to demonstrate that, surprisingly, bringing the lignocellulosic biomass or the cellulose simultaneously into contact with a combination of at least two homogenous catalysts that are different in nature and one or more heterogeneous catalyst(s) in the same reaction chamber being performed under specific operating conditions made it possible to obtain mono-oxidized or poly-oxidized upgradable products directly and to reduce the content of non-upgradable products, such as humins.

SUMMARY OF THE INVENTION

One object of this invention is therefore to provide a process for transformation of lignocellulosic biomass or cellulose into mono-oxidized or poly-oxidized compounds, in which the lignocellulosic biomass or the cellulose is brought into contact, simultaneously, with a combination of at least two homogeneous catalysts and one or more heterogeneous catalyst(s), in the same reaction chamber, in the presence of at least one solvent, with said solvent being water by itself or in a mixture with at least one other solvent, under a reducing atmosphere, and at a temperature of between 50° C. and 250° C., and at a pressure of between 0.5 MPa and 20 MPa, in which At least a first homogeneous catalyst is selected from among the metal salts that may or may not be hydrated, having the general formula $M_mX_n.n'H_2O$ in which M is a metal that is selected from among the metals of groups 3 to 16 of the periodic table, m is an integer of between 1 and 10, n is an integer of between 1 and 10, and n' is an integer of between 0 and 20, and X is at least one anion that is selected from among the halides, the nitrates, the carboxylates, the halocarboxylates, the acetylacetonates, the alcoholates, the phenolates, which may or may not be substituted, the sulfates, the alkyl sulfates, the phosphates, the alkyl phosphates, the halosulfonates, the alkyl sulfonates, the perhaloalkylsulfonates, the bis(perhaloalkylsulfonyl)amides, the arene sulfonates, which may or may not be substituted by halogen or haloalkyl groups, with said anions X able to be identical or different in the case where n is greater than 1, At least a second homogeneous catalyst is selected from among the inorganic or organic Brønsted acids, Said heterogeneous catalyst(s) comprising at least one metal that is selected from among the metals of groups 6 to 11 and the metals of group 14 of the periodic table, and a substrate that is selected from among the oxides of the elements that are selected from among aluminum, titanium, silicon, zirconium, cerium, and niobium, and the mixed oxides that are selected from among the aluminates of zinc, copper, and cobalt, with said oxides able to be doped or not by at least one metal compound that is selected from among tungsten, tin, molybdenum and antimony, taken by themselves or in a mixture, the aluminosilicates that may or may not be crystallized, the aluminophosphates, and the crystallized or amorphous carbon-containing compounds.

In this invention, reference is made to the new notation of the periodic table: Handbook of Chemistry and Physics, 76th Edition, 1995-1996.

In this invention, homogeneous catalyst is defined as a catalyst that is soluble under the operating conditions of the reaction. Heterogeneous catalyst is defined as a catalyst that is not soluble under the operating conditions of the reaction.

One advantage of this invention is to make it possible to obtain mono-oxidized or poly-oxidized upgradable products directly while limiting the formation of non-upgradable products such as the soluble and non-soluble humins, i.e., products of high molecular weight obtained from undesirable condensations of sugars and their derivatives.

Another advantage of this invention is to make possible both the increase of the maximum conversion and the acceleration of the kinetics of conversion of the lignocellulosic biomass or the cellulose by the simultaneous use in the same reaction chamber that operates under a reducing atmosphere of the combination of at least two homogeneous catalysts that are different in nature and one or more heterogeneous catalyst(s) as claimed.

DETAILED DESCRIPTION OF THE INVENTION

The Feedstock

The feedstock that is treated in the process according to the invention is lignocellulosic biomass or cellulose.

Lignocellulosic biomass essentially consists of three natural components that are present in variable quantities according to the origin thereof: cellulose, hemicellulose, and lignin.

Cellulose $(C_6H_{10}O_5)_n$ represents the majority (40-60%) of the composition of lignocellulosic biomass. Cellulose is a linear homopolymer that consists of numerous units of D-anhydroglucopyranose (AGU) that are connected to one another by glycosidic bonds β-(1→4). The repetition unit is the glucose dimer, cellobiose.

Cellulose is insoluble in water at ambient pressure and temperature.

Hemicellulose is the second carbohydrate in quantity after cellulose and constitutes 20 to 40% by weight of lignocellulosic biomass. In contrast to cellulose, this polymer consists for the most part of monomers of pentoses (sugars with 5 carbon atoms) and hexoses (sugars with 6 carbon atoms). Hemicellulose is an amorphous heteropolymer with a degree of polymerization that is less than that of cellulose (30-100).

Lignin is an amorphous macromolecule that is present in lignocellulosic compounds in variable proportions according to the origin of the material (straw ~15%, wood: 20-26%). Its function is mechanical reinforcement, hydrophobization, and support of plants. This macromolecule, rich in phenolic units, can be described as resulting from the combination of three propyl-methoxy-phenol-type monomer units. Its molar mass varies from 5,000 g/mol to 10,000 g/mol for hardwoods and reaches 20,000 g/mol for softwoods.

The lignocellulosic raw material can advantageously consist of wood or plant waste. Other nonlimiting examples of lignocellulo sic biomass material are waste from agricultural operations, such as, for example, straw, grasses, stems, pits, or shells; waste from forestry operations, such as initial cutting products, bark, sawdust, chips, or scraps; products from forestry operations; dedicated crops (short-rotation shrubs); waste from the food-processing industry, such as waste from the industry of cotton, bamboo, sisal, banana, corn, *Panicum virgatum*, alfalfa, coconut, or sugar cane pulp; household organic waste; waste from wood transformation plants, and scrap wood from construction, paper paste, paper that may or may not be recycled.

The feedstock that is used in the process according to the invention is lignocellulosic biomass or cellulose. The cellulose that is used can be crystalline or amorphous. The feedstock of the process according to the invention can also advantageously comprise cellobiose and amorphous polymers of glucose, such as starch. Finally, the feedstock can be saccharose.

The lignocellulosic biomass feedstock can advantageously be used in its raw form, i.e., is made up in its entirety of these three cellulose, hemicellulose and lignin components. The raw biomass generally comes in the form of fibrous waste or powder. It can also advantageously be ground or shredded to allow the transport thereof.

The lignocellulosic biomass feedstock can also advantageously be used in its pretreated form, i.e., in a form that contains at least one cellulosic portion after extraction of lignin and/or hemicellulose.

The biomass preferably undergoes a pretreatment so as to increase the reactivity and the accessibility of cellulose within the biomass before its transformation. These pretreatments are mechanical, thermochemical, thermal-mechanical-chemical and/or biochemical in nature, and bring about the decrystallization of cellulose, a reduction of the degree of polymerization of the cellulose, the solubilization of hemicellulose and/or lignin and/or cellulose, or the partial hydrolysis of hemicellulose and/or cellulose following the treatment.

The lignocellulosic biomass feedstock can also be pretreated so as to be in the form of water-soluble oligomers. These pretreatments are mechanical, thermochemical, thermal-mechanical-chemical and/or biochemical in nature. They bring about the decrystallization and the solubilization of all or part of the cellulose in the form of water-soluble oligomers.

Mechanical treatments go beyond simple shredding because they modify the chemical structure of the components. They improve the accessibility and the reactivity of the cellulose by its decrystallization and by the increase of the exchange surface area. Mechanical treatments include the reduction of the size of the fibers or elementary particles, for example by chipping the biomass with a cutter, by grinding the biomass (adjustment of the grain size), destructuring chips on a press, or grinding by chip abrasion, after preheating. Mechanical treatments can be performed in decentralized mode close to where the biomass is produced or in a centralized mode that directly supplies the transformation.

The thermochemical treatments include the baking of the biomass at high temperature (150-170° C.) in a dilute acid medium (primarily sulfuric acid, but also phosphoric acid, acetic acid, or formic acid), in an alkaline medium (soda, sulfites, lime, . . . ) or in an oxidizing medium (wet oxidation with air or oxygen; peroxide in an alkaline medium; peracetic acid), and in non-conventional media such as ionic liquids (for example, 1-ethyl-3-methylimidazolium acetate [emim][OAc]) or the hydrated inorganic salts ($FeCl_3.6H_2O$, $ZnCl_2.2.5H_2O$) that are used as solvents. The other thermochemical treatments include treatments with solvents (hot ethanol) or roasting that can be defined as pyrolysis at moderate temperature and with a controlled dwell time because it is accompanied by partial destruction of the lignocellulosic material. The known technologies for roasting are, for example, the rotary kiln, the moving bed, the fluidized bed, the heated endless screw, and the contact with metal balls that provide heat. These technologies can optionally use a gas that circulates in co-current or counter-current such as nitrogen or any other inert gas under the conditions of the reaction.

The thermal-mechanical-chemical treatments include vapor treatments (vapor explosion also called flash hydrolysis or "steam explosion"), the AFEX (Ammonia Fiber EXplosion) treatment with ammonia, or the two-screw extrusion with various chemical reagents.

The pretreatment makes it possible to prepare the lignocellulosic biomass by separating the carbohydrate part of the lignin and by adjusting the size of the biomass particles that are to be treated. The size of the biomass particles after pretreatment is generally less than 5 mm, preferably less than 500 microns.

The Catalysts

In accordance with the invention, the lignocellulosic biomass or the cellulose is brought into contact in the process according to the invention, simultaneously, with a combination of at least two homogeneous catalysts that are different in nature as claimed and one or more heterogeneous catalyst(s), in the same reaction chamber, in the presence of at least one solvent, with said solvent being water by itself or in a mixture with at least one other solvent, in a reducing atmosphere, and at a temperature of between 50° C. and 250° C., and at a pressure of between 0.5 MPa and 20 MPa.

An essential criterion of this invention resides in bringing said feedstock into contact, under the operating conditions as claimed, simultaneously, with a combination of at least two homogeneous catalysts that are different in nature as claimed and one or more heterogeneous catalyst(s), within the same reaction chamber.

Actually, the reactions that are brought into play in the process for transformation of the lignocellulosic biomass or the cellulose are not successive reactions because of the use and the simultaneous functioning of a combination of at least two homogeneous catalysts that are different in nature as claimed and one or more heterogeneous catalyst(s), in the same reaction chamber.

The solubilization of the cellulose induced by the homogeneous catalysts and the transformation of the thus dissolved products by the heterogeneous catalyst(s) is therefore done in a concomitant and complementary manner. It is thus possible to take advantage of this compatibility between the homogeneous and heterogeneous catalysts to avoid any intermediate work of treatment or purification, synonymous with additional process costs and significant material losses associated with this stage. Preferably, said process according to the invention is not performed in two successive stages.

Preferably, the lignocellulosic biomass or the cellulose is brought into contact, simultaneously, with a combination of at least two homogeneous catalysts and a heterogeneous catalyst, in the same reaction chamber. In this case, at least two of the homogeneous catalysts are different in nature, i.e., at least a first homogeneous catalyst is selected from among the metal salts that may or may not be hydrated, having as a general formula $M_mX_n.n'H_2O$, in which M, m, n, n' and X have the above-mentioned meaning, and at least a second homogeneous catalyst is selected from among the inorganic or organic Brønsted acids. Thus, in the case where the number of homogeneous catalysts is greater than two, at least two of the homogeneous catalysts are different in nature, with the other catalysts being selected either from among the metal salts that may or may not be hydrated, having for a general formula $M_mX_n.n'H_2O$ in which M, m, n, n' and X have the above-mentioned meaning, or from among the inorganic or organic Brønsted acids, with said other catalysts able to be identical or different within the same nature of catalysts.

In a preferred manner, the lignocellulosic biomass or the cellulose is brought into contact, simultaneously, with a combination of two homogeneous catalysts and a heterogeneous catalyst, in the same reaction chamber.

According to the invention, at least two of the homogeneous catalysts that are used are different in nature.

In accordance with the invention, at least one first homogeneous catalyst is selected from among the metal salts that may or may not be hydrated, having as a general formula $M_mX_n.n'H_2O$ in which M is a metal that is selected from among the metals of groups 3 to 16 of the periodic table, m is an integer of between 1 and 10, n is an integer of between 1 and 10, and n' is an integer of between 0 and 20, and X is at least one anion that is selected from among the halides, the nitrates, the carboxylates, the halocarboxylates, the acetylacetonates, the alcoholates, the phenolates, which may or may not be substituted, the sulfates, the alkyl sulfates, the phosphates, the alkyl phosphates, the halosulfonates, the alkyl sulfonates, the perhaloalkylsulfonates, the bis(perhaloalkylsulfonyl)amides, the arene sulfonates, which may or may not be substituted by halogen or haloalkyl groups, with said anions X able to be identical or different in the case where n is greater than 1.

Said metal M, selected from the groups 3 to 16 of the periodic table of the first homogeneous catalyst according to the invention, is preferably selected from among the following metals: Al, Sc, Ti, V, Cr, Mn, Fe, Co, Ni, Cu, Zn, Ga, Ge, Y, Zr, Nb, Mo, Tc, Ru, Rh, Pd, Ag, Cd, In, Sn, Sb, La, Hf, Ta, W, Re, Os, Jr, Pt, Au, Hg, Tl, Pb, Bi, Po, Ac, Rf, Db, Sg, Bh, Hs, Mt, Ds, Rg, Uub.

In a preferred manner, said metal M is selected from among the following metals: Cr, Mn, Fe, Co, W, Ni, Cu, Zn, Al, Ga, In, and Sn. In a very preferred manner, said metal M is selected from among the metals: Cr, Cu, Fe, Zn, W, Al and Sn.

In accordance with the invention, in the composition of the metal salt, the metal M that is selected from among the cited metals is combined with one or more anion(s) X, which may be identical or different.

Preferably, the anion X is at least one anion that is selected from among the halides, the alkyl sulfonates, the perhaloalkylsulfonates, and the bis(perhaloalkylsulfonyl)amides.

Preferably, the halide is fluoride, chloride, bromide, and iodide.

Preferably, the alkyl sulfonate is mesylate and tosylate.

Preferably, the perhaloalkylsulfonate is triflate.

Preferably, the bis(perhaloalkylsulfonyl)amide is bis(triflimide).

In a very preferred manner, the anion X is a chloride.

Said preferred metal salts comprise metal salts that may or may not be hydrated and that are of general formula $M_mX_n.n'H_2O$, with m, n and n' having the above-mentioned meanings, in which M is a metal that is selected from among the metals Cr, Mn, Fe, Co, W, Ni, Cu, Zn, Al, Ga, In, and Sn, and X is at least one anion that is selected from among the halides, the alkyl sulfonates, the perhaloalkylsulfonates, and the bis(perhaloalkylsulfonyl)amides, with said anions X able to be identical or different in the case where n is greater than 1.

Said very preferred metal salts comprise metal salts that may or may not be hydrated and that are of general formula $M_mX_n.n'H_2O$, with m, n and n' having the above-mentioned meanings, in which M is a metal that is selected from among the metals Cr, Cu, Fe, Zn, W, Al and Sn, and X is at least one anion that is selected from among fluoride, chloride, bromide, iodide, mesylate, tosylate, triflate and bis(triflimide), with said anions X able to be identical or different in the case where n is greater than 1.

A first preferred homogeneous catalyst is the hexahydrated iron chloride metal salt $FeCl_3.6H_2O$.

In the case where several metal salts are used, said metal salts are advantageously selected from among the metal salts that may or may not be hydrated and that are of general formula $M_mX_n.n'H_2O$, with m, n and n' having the above-mentioned meanings, in which M is a metal that is selected from among the metals Cr, Cu, Fe, Zn, W, Al and Sn, and X is at least one anion that is selected from among fluoride, chloride, bromide, iodide, mesylate, tosylate, triflate and bis(triflimide), with said anions X able to be identical or different in the case where n is greater than 1, and with said homogeneous catalysts able to be identical or different.

In accordance with the invention, at least one second homogeneous catalyst is selected from among the inorganic or organic Brønsted acids.

Preferably, the inorganic Brønsted acids are selected from among the following inorganic acids: HF, HCl, HBr, HI, $H_2SO_3$, $H_2SO_4$, $H_3PO_2$, $H_3PO_4$, $HNO_2$, $HNO_3$, $H_2WO_4$, $H_4SiW_{12}O_{40}$, $H_3PW_{12}O_{40}$, $(NH_4)_6(W_{12}O_{40}) \cdot xH_2O$, $(NH_4)_6 Mo_7O_{24} \cdot xH_2O$, $H_3BO_3$, $HClO_4$, $HBF_4$, $HSbF_5$, $HPF_6$, $H_2FO_3P$, $ClSO_3H$, $FSO_3H$, $HN(SO_2F)_2$ and $HIO_3$.

In a preferred manner, the inorganic Brønsted acids are selected from among the following inorganic acids: HCl, $H_2SO_4$, $H_3PO_4$, $H_2WO_3$, $(NH_4)_6(W_{12}O_{40}) \cdot xH_2O$, $(NH_4)_6 Mo_7O_{24} \cdot xH_2O$.

A second very preferred homogeneous catalyst is hydrochloric acid (HCl).

Preferably, the organic Brønsted acids are selected from among the organic acids of general formulas R—COOH, $RSO_2H$, $RSO_3H$, $(RSO_2)NH$, $(RO)_2PO_2H$, ROH where R is a hydrogen or a carbon-containing chain that consists of aryl or alkyl groups that may or may not be substituted by heteroatoms. In a preferred manner, the organic Brønsted acids are selected from among the following organic acids: formic acid, acetic acid, trifluoroacetic acid, lactic acid, levulinic acid, methanesulfinic acid, methanesulfonic acid, trifluoromethanesulfonic acid, bis(trifluoromethanesulfonyl)amine, benzoic acid, paratoluenesulfonic acid, 4-biphenylsulfonic acid, diphenylphosphate, and 1,1'-binaphthyl-2,2'-diyl hydrogen phosphate.

A second very preferred homogeneous catalyst is methanesulfonic acid.

In accordance with the invention, said heterogeneous catalyst(s) comprise(s) at least one metal that is selected from among the metals of groups 6 to 11 and the metals of group 14 of the periodic table, and a substrate that is selected from among the oxides of elements that are selected from among aluminum, titanium, silicon, zirconium, cerium, and niobium, and the mixed oxides that are selected from among the aluminates of zinc, copper and cobalt, with said oxides able to be doped or not by at least one metal compound that is selected from among tungsten, tin, molybdenum, and antimony, taken by themselves or in a mixture, aluminosilicates that may or may not be crystallized, aluminophosphates, and crystallized or amorphous carbon-containing compounds.

Said metal that is selected from among the metals of groups 6 to 11 and the metals of group 14 of the periodic table of the heterogeneous catalyst(s) according to the invention are preferably selected from among the following metals: Cr, Mo, W, Mn, Tc, Re, Fe, Ru, Os, Co, Rh, Ir, Ni, Pd, Pt, Cu, Ag, Au, Zn, Cd, and Hg, on the one hand, and from among: Ge, Sn and Pb, on the other hand, taken by themselves or in a mixture.

In a preferred manner, said metal is selected from among the metals Mo, W, Re, Ru, Co, Rh, Jr, Ni, Pd, Pt, Cu, on the one hand, and Sn, on the other hand, taken by themselves and in a mixture.

In a very preferred manner, said metal is selected from among the metals Ru, Jr, Ni, Pd, Pt, on the one hand, and Sn, on the other hand, taken by themselves and in a mixture.

According to a preferred embodiment, the following mixtures of metals are preferred: NiSn, RePt, FePt, SnPt, CuPt, IrPt, CoPt, RhPt, OsPt, RuRe, PdRe, RuSn and RuPt, and in an even more preferred manner, the following mixtures of metals: NiSn, RePt, RuRe and RuPt.

According to a very preferred embodiment, said metal is platinum.

Preferably, the metal content in said heterogeneous catalyst(s) is advantageously between 0.1% and 10% by weight and in a preferred manner between 0.1 and 5% by weight relative to the total mass of said heterogeneous catalyst(s).

The metal(s) of the heterogeneous catalyst(s) according to the invention are advantageously deposited on a substrate.

In accordance with the invention, said heterogeneous catalyst(s) comprise(s) a substrate that is selected from among the oxides of the elements that are selected from among alumina, titanium, silica, zirconium, cerium, niobium, and the mixed oxides that are selected from among the aluminates of zinc, copper and cobalt, with said oxides able to be doped or not by at least one metal compound that is selected from among tungsten, tin, molybdenum, and antimony, taken by themselves or in a mixture, the aluminosilicates that may or may not be crystallized, the aluminophosphates, and the crystallized or amorphous carbon-containing compounds.

Preferably, the aluminosilicates that may or may not be crystallized are selected from among the zeolites and the mesostructured solids.

Preferably, the crystallized or amorphous carbon-containing compounds are selected from among the activated carbons, the carbon blacks, the carbon nanotubes, the mesostructured carbons, and the carbon fibers.

In the case where said substrate is selected from among the oxides of elements that are selected from among aluminum, titanium, silicon, zirconium, cerium, niobium—doped—a metal element that is preferably selected from among tungsten, tin, antimony, and molybdenum by itself or in a mixture is advantageously added to said substrate. Preferably, the content of the metal element that is selected from among tungsten, tin, antimony, and molybdenum by itself or in a mixture is advantageously between 0.1% and 30% by weight and in a preferred manner between 1 and 20% by weight relative to the total mass of said catalyst.

Said substrate is preferably hydrothermally stable, i.e., stable under conditions that combine water and temperature. Thus, the substrate can undergo a treatment stage whose purpose is to improve its stability under the hydrothermal conditions of the reaction. It is possible to cite, for example, the surface passivation, the deposition of carbon-containing film, and the deposition of oxide.

The deposition of the metal(s) selected from among groups 6 to 11 and the metals of group 14 of the periodic table on said substrate of the heterogeneous catalyst(s) according to the invention in general involves a precursor of the metal(s). For example, it may be a matter of metal organic complexes, metal salts such as metal chlorides, metal nitrates.

The introduction of the metal(s) can advantageously be carried out by any technique that is known to one skilled in the art, such as, for example, ion exchange, dry impregnation, impregnation by excess, vapor phase deposition, etc. The introduction of metal can be done before or after the shaping of the substrate.

The stage for introducing the metal(s) can advantageously be followed by a heat treatment stage. The heat treatment is advantageously carried out between 300° C. and 700° C., under an atmosphere of oxygen or air. The heat treatment stage can be followed by a temperature reduction treatment. The reducing heat treatment is advantageously carried out at a temperature of between 200° C. and 600° C. under a stream or atmosphere of hydrogen.

Preferably, said heterogeneous catalyst(s) also undergo(es) an in-situ reduction stage, i.e., in the reactor where the reaction takes place before the introduction of the reaction feedstock. Said reduction stage can also advantageously be carried out ex-situ.

The heterogeneous catalyst(s) used in this invention can be in the form of powder, extrudates, balls, or pellets. The shaping can be carried out before or after the introduction of the metal.

The heterogeneous catalyst(s) used in this invention is/are characterized by the techniques that are known to one skilled in the art. Transmission microscopy will be cited, for example, to characterize the metal phase.

Transformation Process

In accordance with the invention, the process for transformation of the lignocellulosic biomass or the cellulose is carried out in a reaction chamber in the presence of at least one solvent, with said solvent being water by itself or in a mixture with at least one other solvent, under a reducing atmosphere, and at a temperature of between 50° C. and 250° C., and at a pressure of between 0.5 MPa and 20 MPa.

The process is therefore carried out in a reaction chamber that comprises at least one solvent and in which the feedstock is brought into the presence of the catalytic system according to the invention.

In accordance with the invention, the process according to the invention is performed in the presence of at least one solvent, with said solvent being water by itself or in a mixture with at least one other solvent.

According to a preferred embodiment, the process according to the invention is performed in the presence of water in a mixture with at least one alcohol or at least one organic solvent, under subcritical or supercritical conditions.

The alcohols are advantageously selected from among methanol, ethanol, and propanols.

The organic solvents can advantageously be selected from among tetrahydrofuran and ethyl acetate.

In the case where said process according to the invention is performed in the presence of water mixed with at least one other solvent, the mixture of solvents comprises a content by mass of water that is greater than 5% by weight and in a preferred manner greater than 30%, and in a very preferred manner greater than 50% relative to the total mass of said mixture.

According to another embodiment, the process according to the invention is performed only in the presence of water.

Preferably, the process according to the invention is performed in the presence of at least one solvent with the exception of solvents selected from among the ionic liquids.

In accordance with the invention, the process for transformation of the lignocellulosic biomass or the cellulose according to the invention is carried out under a reducing atmosphere, preferably under a hydrogen atmosphere. The hydrogen can be used in pure form or in a mixture.

Preferably, said process according to the invention is performed at a temperature of between 80° C. and 250° C., and at a pressure of between 2 MPa and 10 MPa.

In general, the process can be performed according to different embodiments. Thus, the process can advantageously be carried out intermittently or continuously, for example in a fixed bed. It is possible to operate in a closed reaction chamber or in a semi-open reactor.

Said homogeneous catalysts are advantageously introduced into the reaction chamber at a rate of a quantity corresponding to a ratio by mass of biomass/homogeneous catalysts of between 1.5 and 1,000, preferably between 5 and 1,000, and in a preferred manner between 10 and 500.

The heterogeneous catalyst(s) is/are introduced into the reaction chamber at a rate of a quantity that corresponds to a ratio by mass of biomass/heterogeneous catalyst(s) of between 1 and 1,000, preferably between 1 and 500, preferably between 1 and 100, preferably between 1 and 50, and also preferably between 1 and 25.

The heterogeneous catalyst(s) introduced into the reactor can undergo a reducing heat treatment stage before the introduction of the reaction feedstock. The reducing heat treatment is preferably carried out at a temperature of between 150° C. and 600° C. under a stream or atmosphere of hydrogen.

The biomass is introduced into the process at a rate of a quantity that corresponds to a ratio by mass of solvent/biomass of between 1 and 1,000, preferably between 1 and 500, and also preferably between 5 and 100.

If a continuous process is selected, the mass speed per hour (mass/heterogeneous catalyst mass feedstock flow rate) is between 0.01 and 5 $h^{-1}$, preferably between 0.02 and 2 $h^{-1}$.

The Products Obtained and the Procedure for Analyzing them

The products of the reaction of the transformation process according to the invention are mono-oxidized or poly-oxidized compounds. Said mono-oxidized or poly-oxidized compounds are water-soluble.

Said mono-oxidized or poly-oxidized compounds advantageously consist of monosaccharides and their derivatives, oligosaccharides, and also soluble polymers that are advantageously formed by successive combinations of the derivatives of monosaccharides.

A carbohydrate that has for a composition $C_nH_{2n}O_n$ where n is greater than 2, obtained by total hydrolysis of cellulose, or hemicellulose, or starch, is referred to by monosaccharides. Monosaccharides are simple sugars that are produced by complete depolymerization of the cellulose and/or hemicellulose, such as, in particular, glucose, galactose, mannose, xylose, fructose, etc.

Monosaccharide derivatives refer to the products that can be obtained by dehydration, isomerization, reduction or oxidation:
  Alcohol sugars, alcohols and polyols: in particular, cellobitol, sorbitol, anhydrosorbitol, hexanetetrols, hexanetriols, hexanediols, xylitol, pentanetetrols, pentanetriols, pentanediols, erythritol, butanetriols, butanediols, glycerol, 1,3-propanediol, propylene glycol, ethylene glycol, hexanols, pentanols, butanols, propanols, ethanol . . .
  Monoketones, polyketones: hydroxyacetone, 2,5-hexanedione . . .
  Carboxylic acids and their esters, lactones: formic acid, alkyl formates, acetic acid, alkyl acetates, hexanoic acid, alkyl hexanoates, levulinic acid, alkyl levulinates, lactic acid, alkyl lactates, glutaric acid, alkyl glutarates, 3-hydroxypropanoic acid, 3-hydroxybutyrolactone, γ-butyrolactone, γ-valerolactone
  Cyclic ethers: for example, tetrahydrofuran (THF), 3-methyltetrahydrofuran (Me-THF) and its positional isomers, 2,4-dimethyltetrahydrofuran and its positional isomers, tetrahydropyran-2-methanol and its positional isomers
  Furans: furan-2,5-dicarboxylic acid, 5-(hydroxymethyl) furfural, furfural . . . .

All of the products that are obtained from the condensation between the monosaccharides, the oligosaccharides and/or the derivatives of monosaccharides are referred to by soluble polymers.

At the end of the reaction, the reaction medium is sampled and centrifuged. The reaction liquid is then analyzed by high-pressure liquid chromatography (HPLC) by using refractometry for determining the content of products of conversion of the aqueous solution.

The quantity of water-soluble reaction products (monosaccharides and derivatives, oligosaccharides, soluble polymers) is determined by the TOC (Total Organic Carbon) analysis that consists in the measurement of carbon in solution. The quantity of monosaccharides and their derivatives is determined by HPLC analyses.

EXAMPLES

In the examples below, the zirconium tungstate catalyst ($ZrO_2$—$WO_x$) is commercial and provided by the MEL Chemical Company and contains 10.3% by weight of tungsten.

Hexahydrated iron chloride is commercial and used without purification.

Example 1

Preparation of the Catalyst C1: 0.5% by Weight of Pt/$ZrO_2$—$WO_x$ (denoted PtZrW)

An aqueous solution of hexachloroplatinic acid $H_2PtCl_6 \cdot xH_2O$ at 1.9% by weight (25 ml, 0.475 g) is added at ambient temperature to the substrate $ZrO_2$—$WO_x$ (24 g) previously desorbed under vacuum (1 hour, 100° C.). The mixture is stirred for one hour and then evaporated. The solid that is obtained is then placed in the oven to dry at 110° C. for 24 hours. The solid is calcined under a stream of dry nitrogen at the temperature of 150° C. for 1 hour, then 250° C. for 1 hour, then 350° C. for 3 hours, and finally 420° C. for 4 hours. It is then reduced under a stream of hydrogen at 500° C. for two hours. The catalyst C1 that is obtained contains 0.5% by weight of platinum.

Example 2

Transformation of Cellulose without a Catalyst (Non-Compliant)

This example relates to the conversion of cellulose without a catalyst for the production of mono-oxidized and poly-oxidized products.

50 ml of water and 1.3 g of SigmaCell® cellulose are introduced into a 100-ml autoclave. The autoclave is heated to 190° C., and a pressure of 5 MPa of hydrogen is introduced. After 24 hours of reaction, the reaction medium is sampled and centrifuged. The reaction liquid is then analyzed by high-pressure liquid chromatography (HPLC) by using refractometry for determining the content of products of conversion of the aqueous solution.

The results that are obtained are referenced in Table 1.

Example 3

Transformation of Cellulose Using $ZrO_2$—$WO_x$ (Non-Compliant)

This example relates to the conversion of cellulose from commercial zirconium tungstate for the production of mono-oxidized and poly-oxidized products.

50 ml of water, 1.3 g of SigmaCell® cellulose, and 0.55 g of zirconium tungstate are introduced into a 100-ml autoclave. The autoclave is heated to 190° C., and a pressure of 5 MPa of hydrogen is introduced. After 24 hours of reaction, the reaction medium is sampled and centrifuged. The reaction liquid is then analyzed by high-pressure liquid chromatography (HPLC) by using refractometry for determining the content of products of conversion of the aqueous solution.

The results that are obtained are referenced in Table 1.

Example 4

Transformation of Cellulose Using Hexahydrated Iron Chloride by Itself (Non-Compliant)

This example relates to the conversion of cellulose from hexahydrated iron chloride for the production of mono-oxidized and poly-oxidized products.

50 ml of water, 1.3 g of SigmaCell® cellulose, and 0.03 g of hexahydrated iron chloride are introduced into a 100-ml autoclave. The autoclave is heated to 190° C., and a pressure of 5 MPa of hydrogen is introduced. After 24 hours of reaction, the reaction medium is sampled and centrifuged. The reaction liquid is then analyzed by high-pressure liquid chromatography (HPLC) by using refractometry for determining the content of products of conversion of the aqueous solution.

The results that are obtained are referenced in Table 1.

Example 5

Transformation of Cellulose Using Hydrochloric Acid by Itself (Non-Compliant)

This example relates to the conversion of cellulose from hydrochloric acid for the production of mono-oxidized and poly-oxidized products.

50 ml of water, 1.3 g of SigmaCell® cellulose, and 0.7 ml of a 0.11 M hydrochloric acid solution are introduced into a 100-ml autoclave. The autoclave is heated to 190° C., and a pressure of 5 MPa of hydrogen is introduced. After 24 hours of reaction, the reaction medium is sampled and centrifuged. The reaction liquid is then analyzed by high-pressure liquid chromatography (HPLC) by using refractometry for determining the content of products of conversion of the aqueous solution.

The results that are obtained are referenced in Table 1.

Example 6

Transformation of Cellulose Using Hexahydrated Iron Chloride and Hydrochloric Acid (Non-Compliant)

This example relates to the conversion of cellulose from hexahydrated iron chloride and hydrochloric acid for the production of mono-oxidized and poly-oxidized products.

50 ml of water, 1.3 g of SigmaCell® cellulose, 0.03 g of hexahydrated iron chloride, and 0.7 ml of a 0.11 M hydrochloric acid solution are introduced into a 100-ml autoclave. The autoclave is heated to 190° C., and a pressure of 5 MPa of hydrogen is introduced. After 24 hours of reaction, the reaction medium is sampled and centrifuged. The reaction liquid is then analyzed by high-pressure liquid chromatography (HPLC) by using refractometry for determining the content of products of conversion of the aqueous solution.

The results that are obtained are referenced in Table 1.

Example 7

Transformation of Cellulose Using the Catalyst C1 (0.5% by Weight of Pt/ZrO$_2$—WO$_x$) (Non-Compliant)

This example relates to the conversion of cellulose from the catalyst C1 that is described in Example 1 for the production of mono-oxidized and poly-oxidized products.

50 ml of water, 1.3 g of SigmaCell® cellulose, and 0.55 g of catalyst C1 introduced under a nitrogen atmosphere are introduced into a 100-ml autoclave. The autoclave is heated to 190° C., and a pressure of 5 MPa of hydrogen is introduced. After 24 hours of reaction, the reaction medium is sampled and centrifuged. The reaction liquid is then analyzed by high-pressure liquid chromatography (HPLC) and in gaseous chromatography (GC) by using refractometry for determining the content of products of conversion of the aqueous solution.

The results that are obtained are referenced in Table 1.

Example 8

Transformation of Cellulose Using the Catalyst C1 (0.5% by Weight of Pt/ZrO$_2$—WO$_x$) in Combination with Hexahydrated Iron Chloride (Non-Compliant)

This example relates to the conversion of cellulose from a combination of the catalyst C1 described in Example 1 and hexahydrated iron chloride for the production of mono-oxidized and poly-oxidized products.

50 ml of water, 1.3 g of SigmaCell® cellulose, 0.03 g of hexahydrated iron chloride, and 0.55 g of catalyst C1 introduced under a nitrogen atmosphere are introduced into a 100-ml autoclave. The autoclave is heated to 190° C., and a pressure of 5 MPa of hydrogen is introduced. After 24 hours of reaction, the reaction medium is sampled and centrifuged. The reaction liquid is then analyzed by high-pressure liquid chromatography (HPLC) by using refractometry for determining the content of products of conversion of the aqueous solution.

The results that are obtained are referenced in Table 1.

Example 9

Transformation of Cellulose Using the Catalyst C1 (0.5% by Weight of Pt/ZrO$_2$—WO$_x$) in Combination with Hydrochloric Acid (Non-Compliant)

This example relates to the conversion of cellulose from a combination of the catalyst C1 that is described in Example 1 and hydrochloric acid for the production of mono-oxidized and poly-oxidized products.

50 ml of water, 1.3 g of SigmaCell® cellulose, 0.7 ml of a 0.11 M hydrochloric acid solution, and 0.55 g of catalyst C1 introduced under a nitrogen atmosphere are introduced into a 100-ml autoclave. The autoclave is heated to 190° C., and a pressure of 5 MPa of hydrogen is introduced. After 24 hours of reaction, the reaction medium is sampled and centrifuged. The reaction liquid is then analyzed by high-pressure liquid chromatography (HPLC) by using refractometry for determining the content of products of conversion of the aqueous solution.

The results that are obtained are referenced in Table 1.

Example 10

Transformation in Two Stages of Cellulose (Non-Compliant)

This example relates to the conversion of cellulose in two successive stages using, in a first stage, hexahydrated iron chloride and hydrochloric acid, and, in a second stage, the catalyst C1 (0.5% by weight of Pt/ZrO$_2$—WO$_x$) for the production of mono-oxidized and poly-oxidized products.

50 ml of water, 1.3 g of SigmaCell® cellulose, 0.03 g of hexahydrated iron chloride, and 0.7 ml of a 0.11 M hydrochloric acid solution are introduced into a 100-ml autoclave. Said homogeneous catalysts are therefore introduced into the reaction chamber at a rate of a quantity corresponding to a ratio by mass of biomass/homogeneous catalysts equal to 40.

The autoclave is heated to 190° C., and a pressure of 5 MPa of hydrogen is introduced. After 24 hours of reaction, the reaction medium is cooled to ambient temperature, and 0.55 g of catalyst C1 is introduced under a nitrogen atmosphere. The autoclave is again heated to 190° C., and a pressure of 5 MPa of hydrogen is introduced. After 24 hours of reaction, the reaction medium is sampled and centrifuged. The reaction liquid is then analyzed by high-pressure liquid chromatography (HPLC) by using refractometry for determining the content of products of conversion of the aqueous solution.

The results that are obtained are referenced in Table 1.

Example 11

Transformation of Cellulose in a Single Stage Using the Catalyst C1 (0.5% by Weight of Pt/ZrO$_2$—WO$_x$) in Combination with Hexahydrated Iron Chloride and Hydrochloric Acid (Compliant)

This example relates to the conversion of cellulose in a single stage from a combination of the catalyst C1 described in Example 1, hexahydrated iron chloride, and hydrochloric acid for the production of mono-oxidized and poly-oxidized products.

50 ml of water, 1.3 g of SigmaCell® cellulose, 0.03 g of hexahydrated iron chloride, 0.7 ml of a 0.11 M hydrochloric acid solution, and 0.55 g of the catalyst C1 introduced under a nitrogen atmosphere are introduced into a 100-ml autoclave.

Said homogeneous catalysts are therefore introduced into the reaction chamber at a rate of a quantity that corresponds to a ratio by mass of biomass/homogeneous catalysts that is equal to 40.

The autoclave is heated to 190° C., and a pressure of 5 MPa of hydrogen is introduced. After 24 hours of reaction, the reaction medium is sampled and centrifuged. The reaction liquid is then analyzed by high-pressure liquid chromatography (HPLC) by using refractometry for determining the content of products of conversion of the aqueous solution.

The results that are obtained are referenced in Table 1.

The conversion is defined as the percentage of solubilization of the biomass or the cellulose in solution and is calculated according to the following equation:

$$\text{Conversion}(\%) = 100 * C_{solubilized}/C_{initial}$$

in which $C_{solubilized}$ represents the quantity of solubilized carbon analyzed by TOC (mg) and $C_{initial}$ represents the quantity of carbon at the beginning of the reaction contained in the biomass or solid cellulose.

The yields of products are calculated by means of HPLC analysis. The yields indicated by a derivative i are calculated as follows:

$$Rdmnt(i) = \frac{C(i) \text{ (g/l)}}{Csolubilisé \text{ (g(C)/l)}} \times \frac{n \times M(C) \text{ (g/mol)}}{M(i) \text{ (g/mol)}}$$

where C(i) represents the concentration of the derivative i determined by HPLC, n represents the number of carbon atoms of the derivative i, M(C) represents the molar mass of the carbon atom, and M(i) represents the molar mass of the derivative.

TABLE 1

Conversion of Cellulose and Formation of Humins

| Examples | Catalyst | Conversion at 6 Hours | Conversion at 12 Hours | Conversion at 24 Hours | Formation of Humins |
|---|---|---|---|---|---|
| 2 | Without Catalyst | 18% | 22% | 25% | + |
| 3 | ZrW | 35% | 42% | 50% | + |
| 4 | FeCl$_3$ | 50% | 52% | 50% | ++ |
| 5 | HCl | 38% | 41% | 47% | ++ |
| 6 | FeCl$_3$ + HCl | 66% | 64% | 55% | +++ |
| 7 | PtZrW (C1) | 37% | 50% | 60% | No Humin |
| 8 | FeCl$_3$ + PtZrW (C1) | 69% | 84% | 92% | No Humin |
| 9 | HCl + PtZrW (C1) | 52% | 61% | 70% | No Humin |
| 10 | 1) FeCl$_3$ + HCl | 66% | 64% | 55% | +++ |
|  | 2) PtZrW (C1) | 54% | 52% | 53% | +++ |
| 11 | FeCl$_3$ + HCl + PtZrW (C1) | 79% | 89% | 95% | No Humin |

The carbon yields of mono-oxidized and poly-oxidized products obtained by transformation of cellulose in the presence of a combination of HCl, FeCl$_3$ and PtZrW (Example 11) are as follows: propylene glycol (10%), 1,2-hexanediol (8%), methanol (5%), 1,2-butanediol (5%), 2-methylpentanol (5%), 1-propanol (4%), ethylene glycol (4%), 3-methyltetrahydrofuran (2%), ethanol (2%), 1,2,6-hexanetriol (1%), erythritol (1%), glycerol (1%), lactic acid (1%), 1,2-pentanediol (1%), 1-pentanol (1%), tetrahydropyran-2-methanol (1%).

The combination of two homogeneous catalysts (hexahydrated iron chloride and hydrochloric acid) and a heterogeneous catalyst (PtZrW) according to the invention proves more effective in comparison with the two homogeneous catalysts taken by themselves or in a mixture and the heterogeneous catalyst taken by itself.

At 6 hours of conversion, starting from the combination of the catalyst C1 described in Example 1, hexahydrated iron chloride and hydrochloric acid (Example 11, compliant), a conversion that is improved by 13% relative to the hexahydrated iron chloride and hydrochloric acid, taken by themselves (Example 6), a conversion improved by 42% relative to the catalyst C1 described in Example 1, taken by itself (Example 7), a conversion improved by 10% relative to hexahydrated iron chloride and the catalyst C1, taken by themselves (Example 8), and a conversion improved by 10% relative to hydrochloric acid and the catalyst C1, taken by themselves (Example 9), are observed.

When the systems that are described in Examples 6 and 7 are used in a process that comprises two successive stages (Example 10), i.e., when hexahydrated iron chloride and hydrochloric acid are used in a first stage and then the catalyst C1 described in Example 1, by itself, is used in a second stage, the maximum conversion is not improved, and the formation of humins is not avoided.

However, when the combination of the catalyst C1 described in Example 1, hexahydrated iron chloride, and hydrochloric acid according to the invention is used for the transformation of the feedstock in a single stage, the maximum conversion reached from this combination (Example 11) is improved by 40% relative to hexahydrated iron chloride and hydrochloric acid, taken by themselves (Example 6), by 35% relative to the catalyst C1 described in Example 1, taken by itself (Example 7), by 3% relative to hexahydrated iron chloride and catalyst C1 described in Example 1, taken by themselves (Example 8), and by 25% relative to hydrochloric acid and the catalyst C1 described in Example 1, taken by themselves (Example 9).

An accelerated conversion kinetics is observed from the combination of the catalyst C1 described in Example 1, hexahydrated iron chloride, and hydrochloric acid relative to hexahydrated iron chloride and hydrochloric acid, taken in combination (Example 6), relative to the catalyst C1 described in Example 1, taken by itself (Example 7), relative to hexahydrated iron chloride and the catalyst C1 described in Example 1, taken by themselves (Example 8) and relative to hydrochloric acid and the catalyst C1 described in Example 1, taken by themselves (Example 9).

Surprisingly, with an increase in the activity of the catalytic system according to the invention and the kinetics of conversion of the cellulose, a total absence of the formation of humins is observed.

The invention claimed is:

1. Process for transformation of lignocellulosic biomass or cellulose into mono-oxidized or poly-oxidized compounds, in which the lignocellulosic biomass or the cellulose is brought into contact, simultaneously, with a combination of at least two homogeneous catalysts and one or more heterogeneous catalyst(s), in the same reaction chamber, in the presence of at least one solvent, with said solvent being water by itself or in a mixture with at least one other solvent, under a reducing atmosphere, and at a temperature of between 50° C. and 250° C., and at a pressure of between 0.5 MPa and 20 MPa, in which At least a first homogeneous catalyst is selected from among the metal salts that may or may not be hydrated, having the general formula $M_nX_n \cdot n'H_2O$ in which M is a metal that is selected from among the metals of groups 3 to 16 of the periodic table, m is an integer of between 1 and 10, n is an integer of between 1 and 10, and n' is an integer of between 0 and 20, and X is at least one anion that is selected from among the halides, the nitrates, the carboxylates, the halocarboxylates, the acetylacetonates, the alcoholates, the phenolates, which may or may not be substituted, the sulfates, the alkyl sulfates, the phosphates, the alkyl phosphates, the halosulfonates, the alkyl sulfonates, the perhaloalkylsulfonates, the bis(perhaloalkylsulfonyl)amides, the arene sulfonates, which may or may not be substituted by halogen or haloalkyl groups, with said anions X able to be identical or different in the case where n is greater than 1, At least a second homogeneous catalyst is selected from among the inorganic or organic Brønsted acids, Said heterogeneous catalyst(s) comprising at least one metal that is selected from among the metals of groups 6 to 11 and the metals of group 14 of the periodic table, and a substrate that is selected from among the oxides of the elements that are selected from among aluminum, titanium, silicon, zirconium, cerium, and niobium, and the mixed oxides that are selected from among the aluminates of zinc, copper, and cobalt, with said oxides being able to be doped or not by at least one metal compound that is selected from among tungsten, tin, molybdenum and antimony, taken by themselves or in a mixture, the aluminosilicates that may or may not be crystallized, the aluminophosphates, and the crystallized or amorphous carbon-containing compounds.

2. Process according to claim 1, in which the metal M of the first homogeneous catalyst is selected from among the following metals: Cr, Mn, Fe, Co, W, Ni, Cu, Zn, Al, Ga, In, and Sn.

3. Process according to claim 1, in which the metal M of the first homogeneous catalyst is selected from among the following metals: Cr, Cu, Fe, Zn, W, Al and Sn.

4. Process according to claim 1, in which the anion X of the first catalyst is at least one anion that is selected from among the halides, the alkyl sulfonates, the perhaloalkylsulfonates, and the bis(perhaloalkylsulfonyl)amides.

5. Process according to claim 1, in which the inorganic Brønsted acids are selected from among the following inorganic acids: HF, HCl, HBr, HI, $H_2SO_3$, $H_2SO_4$, $H_3PO_2$, $H_3PO_4$, $HNO_2$, $HNO_3$, $H_2WO_4$, $H_4SiW_{12}O_{40}$, $H_3PW_{12}O_{40}$, $(NH_4)_6(W_{12}O_{40}) \cdot xH_2O$, $(NH_4)_6Mo_7O_{24} \cdot XH_2O$, $H_3BO_3$, $HClO_4$, $HBF_4$, $HSbF_5$, $HPF_6$, $H_2FO_3P$, $ClSO_3H$, $FSO_3H$, $HN(SO_2F)_2$ and $HIO_3$.

6. Process according to claim 5, in which the second homogeneous catalyst is hydrochloric acid (HCl).

7. Process according to claim 1, in which the organic Brønsted acids are selected from among the organic acids of general formulas R—COOH, $RSO_2H$, $RSO_3H$, $(RSO_2)NH$, $(RO)_2PO_2H$, ROH where R is a hydrogen or a carbon-containing chain that consists of aryl or alkyl groups, which may or may not be substituted by heteroatoms.

8. Process according to claim 7, in which the organic Brønsted acids are selected from among the following organic acids: formic acid, acetic acid, trifluoroacetic acid, lactic acid, levulinic acid, methanesulfinic acid, methanesulfonic acid, trifluoromethanesulfonic acid, bis(trifluoromethanesulfonyl)amine, benzoic acid, paratoluenesulfonic acid, 4-biphenylsulfonic acid, diphenylphosphate, and 1,1'-binaphthyl-2,2'-diyl hydrogen phosphate.

9. Process according to claim 1, in which the metal of the heterogeneous catalyst(s) is selected from among the metals Mo, W, Re, Ru, Co, Rh, Jr, Ni, Pd, Pt, Cu, on the one hand, and Sn, on the other hand, taken by themselves or in a mixture.

10. Process according to claim 1, in which the homogeneous catalysts are introduced into the reaction chamber at a rate of a quantity that corresponds to a ratio by mass of biomass/homogeneous catalysts of between 1.5 and 1,000.

11. Process according to claim 1, in which, in the case where said process is performed in the presence of water in a mixture with at least one other solvent, the mixture of solvents comprises a content by mass of water that is greater than 5% by weight and in a preferred manner greater than 30%, and in a very preferred manner greater than 50% relative to the total mass of said mixture.

12. Process according to claim 1, in which said process is performed only in the presence of water.

13. Process according to claim 1, in which the process is performed in the presence of at least one solvent with the exception of solvents that are selected from among the ionic liquids.

14. Process according to claim 1, in which the reducing atmosphere is a hydrogen atmosphere, pure or in a mixture.

15. Process according to claim 1 that is performed at a temperature of between 80° C. and 250° C., and at a pressure of between 2 MPa and 10 MPa.

* * * * *